United States Patent [19]
Zachmann et al.

[11] Patent Number: 5,510,619
[45] Date of Patent: Apr. 23, 1996

[54] METHOD FOR THE ROUTINE IDENTIFICATION OF PLASTICS

[75] Inventors: Günter Zachmann, Remchingen; Jürgen Gast, Rheinstetten; Arno Simon; Reiner Schübel, both of Karlsruhe, all of Germany

[73] Assignee: Brunker Analytische Messtechnik GmbH, Silberstreifen

[21] Appl. No.: 342,355

[22] Filed: Nov. 18, 1994

[30] Foreign Application Priority Data

Nov. 27, 1993 [DE] Germany ............ 43 40 505.3
Dec. 1, 1993 [DE] Germany ............ 43 40 914.8

[51] Int. Cl.$^6$ ............... G01J 1/00; B07C 5/344
[52] U.S. Cl. ............... 250/339.08; 250/339.11; 250/339.06; 250/339.07; 250/341.8
[58] Field of Search ............ 250/339.08, 339.06, 250/339.07, 339.11, 341.8, 341.5

[56] References Cited

U.S. PATENT DOCUMENTS

| | | |
|---|---|---|
| 3,747,755 | 7/1973 | Senturia .................... 209/111.5 |
| 5,055,695 | 10/1991 | Lange ...................... 250/459.1 |
| 5,134,291 | 7/1992 | Ruhl, Jr. et al. . |
| 5,160,826 | 11/1992 | Cohen et al. . |
| 5,206,510 | 4/1993 | Wolf et al. . |
| 5,214,286 | 5/1993 | Milosevic et al. ............ 250/339.11 |
| 5,225,679 | 7/1993 | Clarke et al. . |
| 5,255,070 | 10/1993 | Pollak et al. . |
| 5,329,127 | 7/1994 | Becker et al. ............... 250/459.1 |
| 5,338,935 | 8/1994 | Truette et al. ............... 250/339.11 |

FOREIGN PATENT DOCUMENTS

| | | |
|---|---|---|
| 0607048 | 7/1994 | European Pat. Off. . |
| 3935617 | 5/1991 | Germany . |
| 2217838 | 11/1989 | United Kingdom . |
| 94/11126 | 5/1994 | WIPO . |

*Primary Examiner*—Constantine Hannaher
*Assistant Examiner*—Virgil O. Tyler

[57] ABSTRACT

A method for routine identification of materials of plastic components with the assistance of infrared spectroscopy with which an infrared reflection spectrum is taken from the surface of a plastic component to be investigated and compared to a set of reference spectra, whereby the material of the plastic component under investigation is correlated to a class of plastic materials represented by one of the reference spectrum, is characterized in that the plastic component under investigation is positioned with the assistance of a video device (25, 26) and in that the infrared reflection spectrum is recorded in the range of the mid-infrared (MIR) in a wave length region between 400 and 4,000 cm$^{-1}$. In this fashion even plastics which, for example, are filled with carbon can be routinely identified. It is preferred when the first derivative of the recorded IR spectrum with respect to wave number is taken and compared to the first derivative of the IR spectra of the reference spectra.

21 Claims, 2 Drawing Sheets

METHOD FOR THE ROUTINE IDENTIFICATION OF PLASTICS

BACKGROUND OF THE INVENTION

The invention concerns a method for the routine identification of the material of plastic components with the assistance of infrared spectroscopy with which an infrared reflection spectrum is taken from the surface of a plastic component under investigation and compared to a set of reference spectra, whereby the material of the plastic component under investigation is correlated to a class of plastic materials represented by one of the reference spectra.

A method of this type is known in the art of near infrared spectrometry from the article by H. Schöpe-Stein in the company magazine "Der Fraunhofer", March 1992, page 29 of the Fraunhofer-Gesellschaft.

With the enormous plurality of currently used plastic components, huge amounts of different kinds of plastic refuse with widely varying properties are continuously produced. In particular, for the purpose of recycling, there is therefore a substantial need for a routine method with which different plastics in refuse can at least be roughly sorted according to class and easily identified. A particularly important application area is thereby the recycling of plastics in the automobile industry.

Towards this end an infrared (IR) spectrometer in the near infrared (NIR: 1,000–2,000 nm corresponding to 4,000–10,000 $cm^{-1}$) region, described in the above mentioned publication is, among others, suitable for this purpose using a fast tunable filter in connection with fast electronics.

An FTIR-spectrometer a well as a method for the taking of reflection spectra from the surfaces of samples in the infrared wave length region is known in the art from U.S. Pat. No. 5,160,826. In particular, a window for an FTIR-spectrometer is described in the publication with which a thin sample layer can be investigated, on the one hand, in the visible region in transmission with the assistance of a microscope component of the spectrometer and, on the other hand, in the infrared region under reflection.

A method and an apparatus for the determination of the physical properties of electronic components comprising semiconductor materials is known in the art from U.S. Pat. No. 5,255,070 with which a test beam of monochromatic light is directed onto the surface of a material sample, whereby the light beam is subjected to a time modulation of the electric vector by means of a modulated pump beam and, whereby the light reflected from the sample surface is detected and analysed.

In plastic identification methods which are also carried out with the assistance of Fourier transformation infrared (FTIR) spectrometers, one works solely in the NIR region since the glass optical components utilized are particularly accessable in this wave number range. In the mid-infrared range (MIR: 400–5,000 $cm^{-1}$), where the window or lens materials are in general hygroscopic salts exhibiting unattractive mechanical properties, the above described method has never been applied. In addition, in contrast to the NIR range, fiber optics is not applicable in the MIR region or usable only under very difficult conditions.

Also for the case of opaque IR plastics, investigations of materials using spectrometers must be carried out in the reflection mode. However, most plastics exhibit strong absorption bands in the MIR region. The light which is reflected from the normally non-planar or rough surfaces has, in addition to a direct scattering component, a significant diffuse scattering portion and multiple reflections occur which, for their part, exhibit a large absorption component. This leads to the fact that MIR spectra of plastics are strongly distorted, exhibit unstable base lines and, in general, tend to resemble the derivative of an IR spectrum. Using such experimental spectra, it is in general not possible to reconstruct a clean "true" absorption spectrum of the relevant material such as one would obtain using absorption spectroscopy of the same substance under laboratory conditions.

These difficulties with the interpretation of the obtained spectra have caused one of average skill in the art to refrain from the consideration of routine investigations of plastics in the MIR range under reflection. With plastics filled with carbon, such as those normally present in motor vehicle parts production, the utilization of spectroscopy in the NIR range is, on the other hand, not possible since NIR spectra capable of analysis cannot be obtained with this type of plastic. For the above mentioned reasons up to this point in time, MIR spectroscopy has been considered to not be suitable as a method for the routine identification of plastics. However, at least a portion of the plastics materials of interest cannot be investigated with conventional NIR spectroscopic methods.

SUMMARY OF THE INVENTION

It is therefore the object of the present invention to present a method of the above mentioned kind with which even plastics filled with carbon as well as other plastic materials which are not accessable to NIR spectroscopy can be investigated in a routine and simple fashion. This purpose is achieved in that the infrared reflection spectrum is recorded in the mid-infrared (MIR) region in a wave number range between 400 and 4,000 $cm^{-1}$.

The procedure for recording an MIR reflection spectra proposed in accordance with the invention is surprisingly well suited for the above described purpose of routine investigation of plastics since, namely, a "clean" spectrum is not necessary if only plastic materials or classes of plastics are to be identified. Rather it is sufficient for the measurement to provide reproduceable and unique information which, in some kind of manner, is characteristic of the plastic material being investigated. This is, however, also possible in the mid-infrared range so that, in particular with plastics filled with carbon, it can be utilized in a routine investigation for the purposes of identification.

In a preferred embodiment of the method, the spectrum at least includes the MIR range of 600–3,600 $cm^{-1}$. Nearly the maximum possible amount of information is assembled in this fashion.

In a simpler embodiment the spectrum includes only a partial MIR range of less than 1,000 wave numbers. In this fashion a recorded spectrum requires less memory, the spectrum recording time is reduced, and optical elements can be utilized which are specially tailored to particular materials under investigation (detectors, filters, windows with reduced working ranges and the like).

An embodiment of the method in accordance with the invention is particularly preferred with which, prior to the comparison with the reference spectrum, a preferentially first derivative of the recorded IR spectrum with respect to wave number is taken and corresponding derivatives of the IR spectra of the reference substance are also utilized as reference spectra. By limiting the measuring region to the information containing evaluation region (precisely the range where the plastics absorb) it is possible to substantially improve the quality of the identification.

In a further advantageous embodiment, within the context of a series of measurements of a plurality of plastic components, only, in each case, one initial measurement of an IR reflection spectrum in the near IR range is recorded and compared with reference spectra and only with plastic components with which this first measurement does not lead to an unique identification, is a second measurement in the middle IR range subsequently carried out. In this fashion, plastic refuse can be automatically identified according to an automated sorting procedure in a standard fashion rapidly, in the range of milliseconds, using a "cheap" NIR measurement and more or less fully automatically sorted on a conveyor belt. "Odd" materials or those which cannot be correlated in this fashion can then be sorted out and introduced into the relatively expensive and slower MIR measurement ($\approx 1$ second). Such a sorting installation could then possibly also exhibit a reduced degree of automisation in the MIR region, since substantially smaller quantities of plastic components gain entrance thereto.

A variation of the above mentioned method is particularly economical with which both measurements (in the NIR and in the MIR ranges) are carried out sequentially or even simultaneously with the same IR spectrometer.

In an alternative variation of this method, both measurements in the NIR and in the MIR ranges are carried out with two separate IR spectrometers. In this fashion, the entire method can be made faster which increases the throughput of the plastic components under investigation and thereby makes the method more economical.

An embodiment of the method in accordance with the invention is preferred with which the MIR spectrum is taken with the assistance of a Fourier transformation infrared (FTIR) spectrometer. This procedure, in addition to the utilization of other general advantages of Fourier spectrometers such as, for example, the possibility of "multiplexing", the very rapid data acquisition, and the significantly improved properties at large wave length compared to dispersive spectrometers, also has the special advantage that no CCD arrays are necessary for recording the spectra which, in particular, are not available in the MIR and FIR regions.

A variation of this method is particularly preferred with which, during the measurement, a first infrared (IR) beam is deflected out of the FTIR spectrometer through a window which is transparent in the mid-infrared and is focussed onto a surface region of the plastic component under investigation, whereby the IR light reflected from the surface forms a second IR beam and is focussed through the same or through a second window onto a detector for mid-infrared which is within the FTIR spectrometer. In this fashion, the method can also be utilized with very rapid sample changes, for example, on a conveyor belt, whereby external configuration of the sample under investigation by routine measurements outside the spectrometer is almost certainly required.

In an additional advantageous variation, surface coatings which may be located at the surface region of the plastic component being investigated are first removed prior to the measurement since such a coating, for example paint or the like, can be optically opaque and can absorb IR light and/or produce an interfering spectrum.

In order to better define the mirrored reflection, a variation provides that a flat surface is produced in the surface region of the object to be investigated prior to the measurement.

In a further improved variation, one provides that the plastic component under investigation is oriented in such a fashion that the IR light which is mirror reflected from the surface region impinges along the second IR beam onto the detector. The IR measurement, in mirror reflection, can also be better defined in this manner.

A particularly preferred variation of the method in accordance with the invention is characterized in that the IR light, departing from an IR light source, preferentially, a spiral-wound filament or a so-called glow-bar, first passes through an interferometer in the FTIR spectrometer and then, in the form of a first light beam, is focussed through the first window onto the surface region of the plastic component under investigation. The utilization of an MIR source has the advantage that the light beam utilized for the measurement exhibits a substantially reduced intensity compared to "white" light. This type of white light must be initially irradiated onto the sample and then into the interferometer which, for example, could lead to a heating-up of the sample.

An FTIR spectrometer for carrying out the above described method is also within the framework of the invention with which a first and a second MIR transparent window are provided for, and the axes of the first and second IR beams are each perpendicular to the surfaces of the first and the second windows respectively. In contrast to IR spectrometers known in the art, the apparatus in accordance with the invention exhibits two MIR transparent windows by means of which, in contrast to the solution having only one window, reflections, which could possibly contribute signal background in excess of the weak reflection signal of the measured plastic component, are reduced. With the simple single window solution the beam axes must impinge on the window at an angle, which leads to higher reflection losses.

An embodiment of the FTIR spectrometer in accordance with the invention is particularly preferred with which the angle between the axes of both beams lies in range between 5° and 30° and preferentially between 10° and 20°. In this fashion, despite the finite radial extent of the utilized beam, as perpendicular as possible an incidence of the measuring light onto the sample surface under investigation and a corresponding nearly perpendicular reflection from the surface are guaranteed.

An embodiment is also preferred with which the window comprises one of the materials KBr, KCl, ZnSe, KRS5, $CaF_2$, $MgF_2$. This type of MIR transparent window is easily available commercially.

Likewise advantageous is an embodiment of the FTIR spectrometer in accordance with the invention with which the detector is a DTGS detector (deuterated triglycine sulfate). These MIR detectors are commercially available.

An embodiment of the FTIR spectrometer in accordance with the invention is particularly preferred with which the plastic component under investigation is positioned with the assistance of a video apparatus. By positioning the plastic component under investigation using a video apparatus one guarantees, in an operator-friendly fashion, that the sample is located at the correct measuring position, which is the fundamental requirement for problem-free routine measurement. In a preferred improvement of this embodiment an endoscope with an attached video camera constitutes the video device.

The endoscope can be positioned between both windows or between the incident and exit mirrors of the spectrometer and is oriented preferentially perpendicular to the plastic component under investigation. The video camera is then connected to the end of the endoscope facing away from the window and facilitates observation of the measuring sample and localization of the processed measuring location on the measuring sample to allow the operator to bring this location, in as correct a manner as possible, into the measuring position.

A particularly compact embodiment is one in which the plastic component under investigation can be illuminated via the endoscope for purposes of positioning. Alternatively, in another embodiment, an illumination device for the illumination of the measuring sample can be provided for between the windows of the spectrometer.

Finally, another embodiment is advantageous with which additional visualizing devices are provided for with which the plastic component under investigation can be observed from the measuring position. In this fashion, a more rapid and more precise positioning of the measuring sample is possible.

Further advantages of the invention can be derived from the description and the accompanying drawing. The above mentioned features as well as those which are to be described below can also be utilized in accordance with the invention individually or collectively in arbitrary combination. The embodiment mentioned is not to be considered as an exhaustive enumeration, rather has exemplary character only.

The invention is represented in the drawing and will be more closely described and explained with a concrete embodiment.

BRIEF DESCRIPTION OF THE DRAWING

FIG. 1b shows a side view of the spectrometer assembly of FIG. 1a;

DESCRIPTION OF THE PREFERRED EMBODIMENT

Figure 1A:
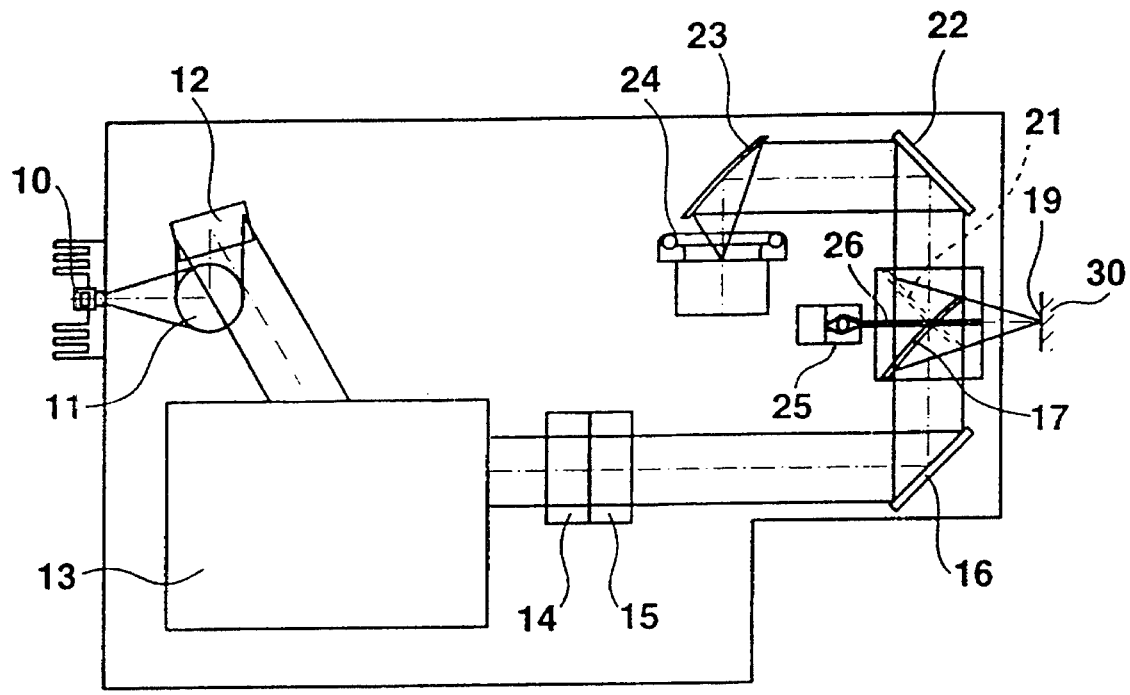
FIG. 1a shows a plan view of an infrared spectrometer assembly for carrying out the method in accordance with the invention.
Figure 1B:
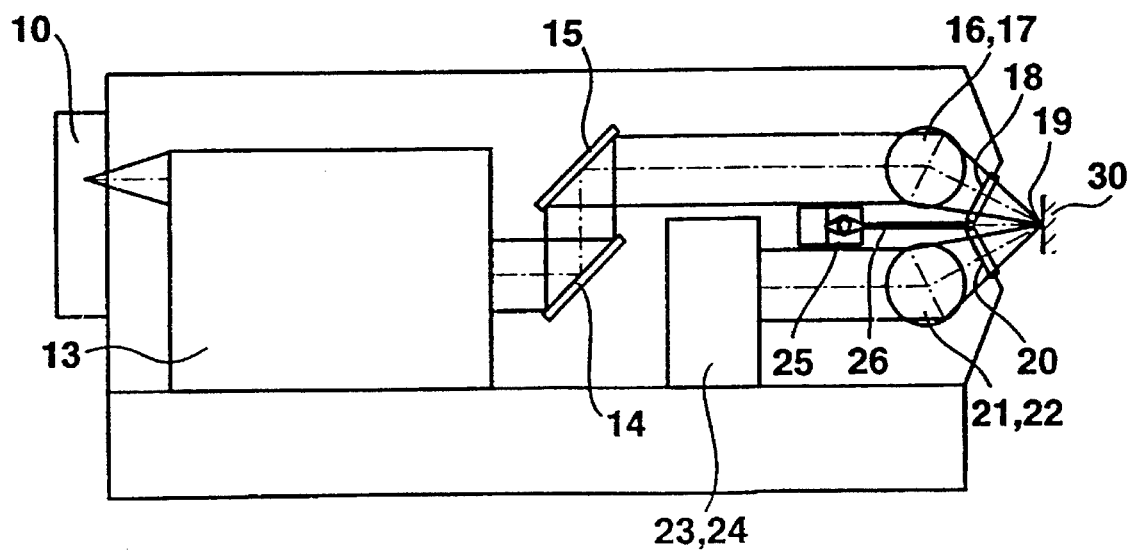

The Fourier transform infrared (FTIR) spectrometer shown in FIG. 1a and FIG. 1b exhibits the following optical path:

Infrared light from an IR light source 10, preferentially a spiral-wound filament or a so-called glowsbar, is incident on concave mirror 11 and is reflected therefrom via a planar mirror 12 into an interferometer 13. After passing through the interferometer 13, the height of the infrared beam is displaced via two planar mirrors 14, 15 and it is sidewardly deflected via an additional planar mirror 16 and, with the assistance of a concave mirror 17, focussed through a first MIR transparent window 18 onto the focal spot 19 at a first planar surface 30 of a measuring sample. The reflected MIR light passes through a second MIR transparent window 20 to once again enter into the spectrometer and is projected onto a planar mirror 22 by means of an additional concave mirror 21, and therefrom deflected onto a concave mirror 23 to finally be focussed onto and detected by an MIR detector 24. The angle between the axes of the first IR beam exiting through the first window 18 and the second beam again entering into the spectrometer through the second window 20, assumes a value between 5° and 30°, preferentially between 10° and 20°. In this fashion, on the one hand, interfering reflections on the surfaces of the entrance and exit windows are avoided which, under certain circumstances, could significantly interfere with the recorded spectrum and, on the other hand, both the incident as well as the exiting beams are directed largely perpendicularly to the surface 30 of the sample. In addition, the plastic component to be investigated is oriented in such a fashion that the IR light mirror-reflected from the surface region 30 gains entrance via the second IR beam through the second window 20 onto the detector 24. If necessary, a flat surface 30 is produced on the surface region of the plastic component under investigation prior to the measurement. Possible surface coatings are removed from the plastic component before the measurement.

It is necessary to guarantee that the processed location of the sample is brought into the measurement position. Towards this end, the sample to be analysed is observed from the back by means of a video device so that the operator can correctly position the sample.

The observational device preferentially comprises an endoscope 26 with a connected video camera 25. The endoscope 26 can be positioned between the two mirrors 17, 21 or windows 18, 20 and is preferentially oriented perpendicular to the sample to be positioned. A video camera 25, connected to the back end of the endoscope 26, allows for the observation of the sample and localization of the processed measurement location on the sample, and permits the operator to bring this location into the measuring position.

An illumination unit, attached between the windows 18, 20, can be switched on to illuminate the sample during its positioning. Alternatively, the sample can be illuminated via the endoscope 26.

Other visual devices are also conceivable to allow for observation of the sample from the measuring position so that the operator can correctly position the sample.

The windows 18, 20 can, for example, comprise the materials KBr, KCl, ZnSe, KRS5, $CaF_2$, $MgF_2$. The MIR detector 24 is preferentially a DTGS (deuterated triglycine sulfate) detector.

Using the above described FTIR spectrometer in accordance with the invention, it is possible to carry out a high-quality automated method for the routine identification of materials of plastic components with which an infrared spectrum in the mid-infrared (MIR) range is recorded in a wave number region between 400 and 4,000 $cm^{-1}$ of the flat surface 30 of the plastic component under investigation. This spectrum is compared with a set of reference spectra previously obtained from known sample materials. In this fashion the material of the plastic component under investigation can easily be correlated to a class of plastic materials represented by one of the reference spectra, whereby plastics which are filled with carbon can also be easily investigated in this fashion. The utilized Wave number region in the MIR can, in particular, also include less than 1,000 wave numbers so that the spectra produced require a relatively small amount of memory and a correspondingly reduced measuring time. In addition, with a restricted region, special materials can be utilized for the optical elements (detector, filter, window and the like).

When comparing the recorded spectrum with the reference spectrum, it is preferred when a derivative of the spectrum, in general the first derivative with respect to wave number, is taken and compared to the corresponding derivative of the reference IR spectrum. In this fashion the reflected infrared radiation, normally leading to the occurrence of base line problems, vanishes or is changed in such a fashion that the spectral distortion is less noticeable during analysis for the purpose of identifying the measured plastic.

Of course in this fashion, a portion of the entire information content of the measured spectrum is also lost which, however, can be easily accepted. Whereas the original spectrum more closely resembles a dispersion spectrum or a first derivative of an absorption spectrum, the first derivative with respect to wave number usually strongly resembles the conventional absorption spectrum. This, as mentioned above, can be compared to reference spectra, obtained in a similar fashion and stored in the spectrometer, with the assistance of conventional algorithms. The first derivative is effectively utilized, since it eliminates the long wave length base line disturbances largely caused by the morphology of the sample and the remaining "fine" information is nevertheless sufficiently characteristic of the sample material being identified. In special cases, use of the second derivative of the spectrum can also be advantageous.

Figure 2A:
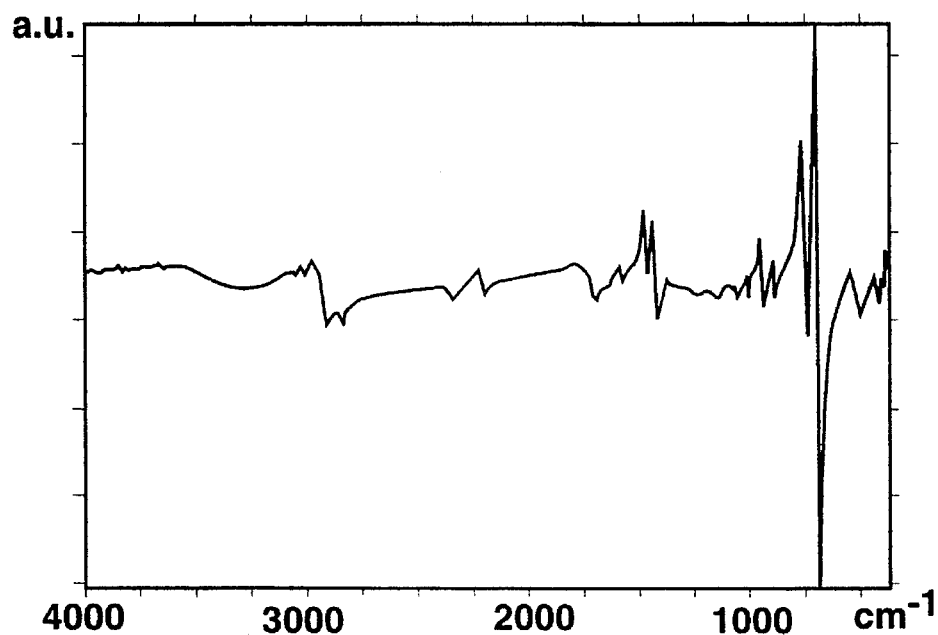
FIG. 2a shows an ABS plastic spectrum.
Figure 2B:
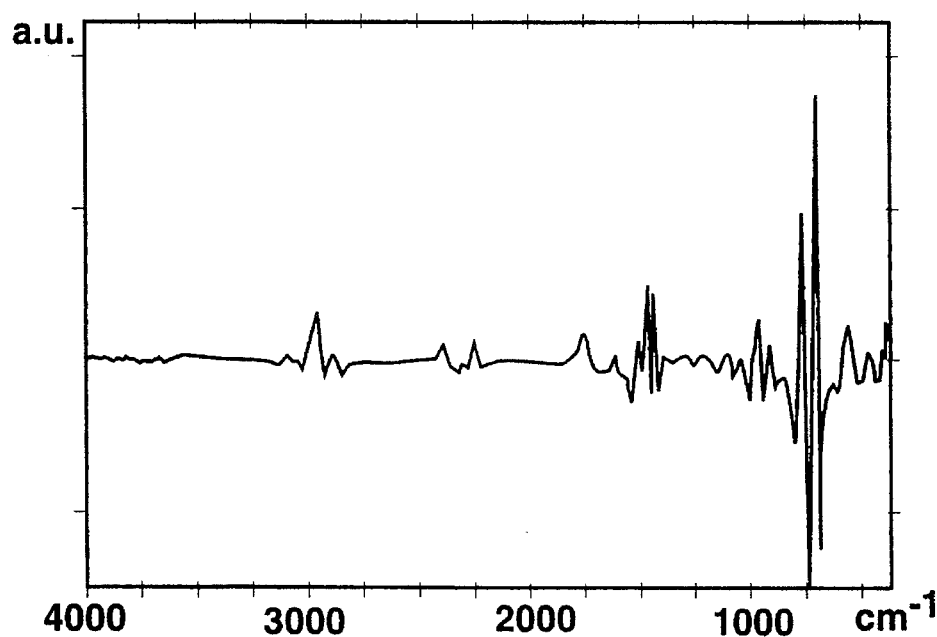
FIG. 2b shows the first derivative of the spectrum of FIG. 2a with respect to wave number.

For the purposes of illustration, FIG. 2a shows an original spectrum of a ABS (acrylic-butadiene-styrene) plastic in arbitrary units plotted against wave number. FIG. 2b shows the first derivative of the original spectrum shown in FIG. 2a. As can be seen, structures characteristic of the sample material can be significantly better enhanced by the first derivative. The examples shown also suggest that it is conceivable to only utilize a partial region of, for example, several hundred wave numbers for identification rather than measuring and evaluating the entire MIR region.

The routine method in accordance with the invention for the identification of materials of plastic components can largely be carried out as follows:

a) select the plastic component to be investigated
b) select the surface region to be investigated
c) removal of a coating or a paint layer if necessary
d) generate, if necessary, a flat surface perhaps in connection with method step c)
e) placing this surface into the measuring position (focal spot 19) of an MIR beam exiting through the first window 18 of the FTIR spectrometer
f) orienting the surface 30 in such a fashion that the reflected beam again gains entrance through the second window 20 into the spectrometer to impinge on the MIR detector 24
g) measuring the MIR spectrum with the assistance of the FTIR spectrometer
h) forming the first derivative of the measured spectrum with respect to wave number
i) comparing the derivative spectrum to a corresponding derivative of a plurality of stored reference spectra
j) correlating the material of the measured plastic component to a reference spectrum and thereby to a particular class of material Within the framework of a series of measurements of a plurality of plastic components to be identified an IR reflection spectrum can, in each case, be taken in an initial measurement in the near infrared region (NIR) and compared to the corresponding reference spectra. Only in the event of plastic components by which this first measurement does not lead to an unique identification, is a subsequent second measurement in the mid-infrared range (MIR) necessary. In this fashion the rapid and thereby inexpensive NIR measurement can be carried out in the majority of cases as the sole measurement and the corresponding pieces can be more or less completely automatically sorted on a conveyor belt. Materials with which a first measurement does not lead to a correlation can be sorted out and introduced into a slower and therefore somewhat more expensive MIR measurement. This can, possibly, be subject to a reduced degree of automation since there are a substantially lower number of components under investigation.

In order to reduce apparative expense and difficulty, it is possible for both measurements in the NIR and in the MIR ranges to be carried with the same FTIR spectrometer, simultaneously or successively. Alternatively, both measurements can be carried out with two separate spectrometers to correspondingly accelerate the entire process.

We claim:

1. An infrared spectroscopy method for the routine identification of a plastic component in refuse for the purpose of recycling, comprising the steps of:
    a) taking an IR reflection spectrum of the plastic component in the near infrared range (NIR) of wave numbers between 4,000 and 10,000 cm$^{-1}$;
    b) comparing the spectrum of step a) to reference spectra;
    c) selecting the plastic component if steps a) and b) do not lead to a unique identification;
    d) guiding light from a mid-infrared range (MIR) source having a wave number range between 400 and 4000 cm$^{-1}$ through a Fourier transform infrared (FTIR) spectrometer;
    e) focussing the light of step d) onto a surface region of the plastic component selected in step c);
    f) passing light reflected from the surface region through onto a mid-infrared detector;
    g) recording an MIR spectrum of the selected plastic component;
    h) comparing the MIR spectrum to a set of reference spectra having a plurality of member spectra, each member spectrum corresponding to a class of plastic materials; and
    i) correlating the selected plastic component to one member spectrum of one class of plastic materials.

2. The method of claim 1, wherein the spectrum includes at least the MIR range between 600 to 3,600 cm$^{-1}$.

3. The method of claim 1, wherein the spectrum spans an MIR range of less than 1,000 cm$^{-1}$.

4. The method of claim 1, wherein prior to the comparison with the reference spectra, a first derivative of the recorded IR spectrum with respect to wave number is taken and a corresponding derivative of the IR spectrum of reference substances is likewise utilized.

5. The method of claim 1, wherein both measurements in the NIR and MIR ranges are carried out with the same IR spectrometer, simultaneously or sequentially.

6. The method of claim 1, wherein the two measurements in the NIR and MIR ranges are carried out with two separate IR spectrometers.

7. The method of claim 1, wherein a surface coating present in the surface region of the plastic component under investigation is removed.

8. The method of claim 1, wherein before the measurement, a flat surface is produced in the surface region of the plastic component under investigation.

9. The method of the claim 1, wherein the plastic component under investigation is oriented in such a fashion that the IR light mirror-reflected from the surface region impinges via the second IR beam onto the detector.

10. An FTIR spectrometer for carrying out the method according to claim 1, wherein axes of the first and the second IR beams are each perpendicular to surfaces of the first and second windows respectively.

11. The FTIR spectrometer according to claim 10, wherein the angle between the axes of the two beams lies between 5° and 30°.

12. The FTIR spectrometer according to claim 10, wherein the windows comprise one of the materials KBr, KCl, ZnSe, KRS5, $CaF_2$, $MgF_2$.

13. The FTIR spectrometer according to claim 10, wherein the detector is a DTGS detector (deuterated triglycine sulfate).

14. The FTIR spectrometer according to claim 10, wherein the plastic component to be investigated is positioned with the assistance of the video device.

15. The FTIR spectrometer according to claim 14, wherein an endoscope with an attached video camera is provided for as the video device.

16. The FTIR spectrometer according to claim 14, wherein an endoscope is positioned between the two windows and is oriented perpendicularly to the plastic component to be investigated.

17. The FTIR spectrometer according to claim 14, wherein the plastic component to be investigated can be illuminated via an endoscope for purposes of positioning.

18. The FTIR spectrometer according to claim 14, wherein the plastic component to be investigated can be illuminated for purposes of positioning by an illumination device provided between the two windows.

19. The FTIR spectrometer according to claim 14, wherein additional visualization devices are provided for by means of which the plastic component to be investigated can be observed from the direction of the measuring position.

20. An infrared spectroscopy method for the routine identification of a plastic component in refuse for the purpose of recycling comprising the steps of:

a) taking an IR reflection spectrum of the plastic component in the near infrared range (NIR) of wave numbers between 4,000 and 10,000 $cm^{-1}$;

b) comparing the spectrum of step a) to reference spectra;

c) selecting the plastic component if steps a) and b) do not lead to a unique identification;

d) guiding light from a mid-infrared range (MIR) source having a wave number range between 400 and 4000 $cm^{-1}$ through a Fourier transform infrared (FTIR) spectrometer;

e) focussing the light of step d) as a first light beam through a first MIR transparent window in a direction perpendicular to a plane of the first window onto a surface region of the plastic component selected in step c);

f) passing light reflected from the surface region as a second light beam through a second MIR transparent window in a direction perpendicular to a plane of the second window onto a mid-infrared detector within the FTIR spectrometer, the first and second light beams having an opening angle between 5° and 30°;

g) recording an MIR spectrum of the selected plastic component;

h) comparing the MIR spectrum to a set of reference spectra having a plurality of member spectra, each member spectrum corresponding to a class of plastic materials; and i) correlating the selected plastic component to one member spectrum of one class of plastic materials.

21. An infrared spectroscopy method for the routine identification of a plastic component in refuse for the purpose of recycling comprising the steps of:

a) taking an IR reflection spectrum of the plastic component in the near infrared range (NIR) of wave numbers between 4,000 and 10,000 $cm^{-1}$;

b) comparing the spectrum of step a) to reference spectra;

c) selecting the plastic component if steps a) and b) do not lead to a unique identification;

d) positioning the selected plastic component with a video device, the video device comprising an endoscope and video camera;

e) guiding light from a mid-infrared range (MIR) source having a wave number range between 400 and 4000 $cm^{-1}$ through a Fourier transform infrared (FTIR) spectrometer;

f) focussing the light of step d) as a first light beam through a first MIR transparent window in a direction perpendicular to a plane of the first window onto a surface region of the plastic component selected in step c);

g) passing light reflected from the surface region as a second light beam through a second MIR transparent window in a direction perpendicular to a plane of the second window onto a mid-infrared detector within the FTIR spectrometer, the first and second light beams having an opening angle between 5° and 30°;

h) recording an MIR spectrum of the selected plastic component;

i) comparing the MIR spectrum to a set of reference spectra having a plurality of member spectra, each member spectrum corresponding to a class of plastic materials; and j) correlating the selected plastic component to one member of one class of plastic materials.

* * * * *